(12) United States Patent
Borowitz et al.

(10) Patent No.: US 7,792,580 B2
(45) Date of Patent: Sep. 7, 2010

(54) IMPLANTABLE MEDICAL DEVICE WITH HIS-PURKINJE ACTIVITY DETECTION

(75) Inventors: Lynn A. Borowitz, Roseville, MN (US); William J. Combs, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 1181 days.

(21) Appl. No.: 10/945,620

(22) Filed: Sep. 21, 2004

(65) Prior Publication Data
US 2006/0064027 A1   Mar. 23, 2006

(51) Int. Cl.
*A61N 1/362* (2006.01)
(52) U.S. Cl. .......................................................... 607/9
(58) Field of Classification Search ......... 600/508–509, 600/373, 374, 377, 393, 513; 607/4–6, 9, 607/116, 119, 123
See application file for complete search history.

(56) References Cited

U.S. PATENT DOCUMENTS

| | | | | |
|---|---|---|---|---|
| 4,261,369 A | * | 4/1981 | Allor | ........................... 600/508 |
| 4,316,472 A | | 2/1982 | Mirowski et al. | |
| 4,375,817 A | | 3/1983 | Engle et al. | |
| 4,384,585 A | | 5/1983 | Zipes | |
| 4,448,202 A | * | 5/1984 | Wajszczuk et al. | .......... 600/522 |
| 4,577,633 A | | 3/1986 | Berkovits et al. | |
| 4,587,970 A | | 5/1986 | Holley et al. | |
| 4,726,380 A | | 2/1988 | Vollmann | |
| 4,727,380 A | | 2/1988 | Miura et al. | |
| 4,727,877 A | | 3/1988 | Kallok | |
| 4,751,931 A | * | 6/1988 | Briller et al. | ................ 600/513 |
| 4,785,815 A | | 11/1988 | Cohen | |
| 4,800,883 A | | 1/1989 | Winstrom | |
| 4,830,006 A | | 5/1989 | Haluska | |
| 4,880,005 A | | 11/1989 | Pless et al. | |
| 4,949,719 A | | 8/1990 | Pless et al. | |
| 4,953,551 A | | 9/1990 | Mehra | |
| 5,117,824 A | | 6/1992 | Keimel et al. | |
| 5,163,427 A | | 11/1992 | Keimel et al. | |
| 5,188,105 A | | 2/1993 | Keimel | |
| 5,345,362 A | | 9/1994 | Winkler | |

(Continued)

FOREIGN PATENT DOCUMENTS

EP    0494487 A2    7/1992

(Continued)

OTHER PUBLICATIONS

Borowitz, et al., "Detection of His-Purkinje Activity from Distant Intracardiac Electrograms", Indiana University Purdue University, Indianapolis, Indiana and Medtronic, Inc., Minneapolis, Minnesota.

(Continued)

*Primary Examiner*—Carl H Layno
*Assistant Examiner*—Frances P Oropeza
(74) *Attorney, Agent, or Firm*—Stephen W. Bauer

(57) ABSTRACT

Implantable medical devices having two or more leads can utilize digital signal processing to sample and filter the acquired data. The processed data is utilized to identify electrical activity in cardiac tissue remote from the lead location. An atrial lead and a ventricular lead are used to acquire data and the data is processed to indicated electrical timing within the HIS bundle.

12 Claims, 9 Drawing Sheets

U.S. PATENT DOCUMENTS

| | | | |
|---|---|---|---|
| 5,355,891 A * | 10/1994 | Wateridge et al. | 600/515 |
| 5,501,702 A * | 3/1996 | Plicchi et al. | 607/20 |
| 5,531,768 A * | 7/1996 | Alferness | 607/6 |
| 5,685,317 A * | 11/1997 | Sjostrom | 600/528 |
| 5,741,308 A | 4/1998 | Sholder | |
| 5,776,072 A * | 7/1998 | Hsu et al. | 600/518 |
| 6,424,865 B1 * | 7/2002 | Ding | 607/9 |
| 6,456,878 B1 * | 9/2002 | Yerich et al. | 607/9 |
| 6,609,027 B2 * | 8/2003 | Kroll et al. | 607/9 |
| 6,931,273 B2 * | 8/2005 | Groenewegen et al. | 600/515 |
| 7,228,174 B2 * | 6/2007 | Burnes et al. | 607/17 |
| 2003/0105492 A1 * | 6/2003 | Ding et al. | 607/9 |

FOREIGN PATENT DOCUMENTS

| | | |
|---|---|---|
| EP | 1234597 A2 | 2/2002 |
| WO | 92/18198 | 11/1992 |
| WO | 97/22380 | 6/1997 |

OTHER PUBLICATIONS

Kinney et al., Comprehensive Cardiac Care, 8th Edition: pp. 166, 169-171; Mosbey-Year Book, Inc.; St. Louis, Missouri; 1996.

Park, "Analysis of Non-Invasively Recorded His-Purkinje Singals From . . . ", http://Master of Science Thesis, Indiana University Purdue University, Indianapolis.

James, "Structure and Function of the Sinus Node, AV Node and His . . .", http://Progress in Cardiovascular Diseases.

Macdonald, "A Software Trigger for Intracardiac Waveform Detection with Automatic Threshold Adjustment", pp. 167-170, University of Michigan, Ann Arbor, Michigan, IEEE-0276-6574.

LeBlanc, "Improved Beat-to-Beat Timing Measurements of His-Bundle signal", pp. 1168-1177, IEEE Transactions on Biomedical Engineering, vol. 41, No. 12, Dec. 1994.

* cited by examiner

IMPLANTABLE MEDICAL DEVICE WITH HIS-PURKINJE ACTIVITY DETECTION

BACKGROUND OF THE INVENTION

The present invention relates to implantable medical devices. More specifically, the present invention relates to implantable medical devices having one or more sensors positioned within a heart.

DESCRIPTION OF THE RELATED ART

The cardiac cycle is typically initiated by a depolarization occuring within the sinoatrial (SA) node. The depolarization wave front or action potential propagates around the atria and into the atrioventricular (AV) node. Propagation through the AV node is delayed to provide sufficient time for contraction of the atria prior to initiating ventricular contraction. The action potential continues to propagate and enters the HIS bundle and propagation continues at an increased rate. The HIS bundle divides into the left and right bundle branches, which in turn, include Purkinje fibers extending around the left and right ventricular walls. The HIS bundle interconnects the AV node with the septum. The left and right bundle branches extend within the septal wall and diverge proximate the apex toward the left and right ventricles.

As such, the depolarization wave front travels along the septum and diverges proximate the apex. Thus, substantive contraction of the ventricles occurs proximate the apex and progress towards the base.

The timing of cardiac cycles is beneficially variable. As demand increases, cardiac output is correspondingly increased. One direct mechanism for achieving increased output is to increase the cardiac rate. Implicitly, depolarization occurs more frequently; thus, intervals between depolarizations decrease. Various intervals within a given cycle will also decrease. For example, the AV delay may shorten somewhat while permitting sufficient contraction of the atria prior to ventricular contraction.

While variations in timing are of benefit, various conditions exist where timing variations disrupt cardiac performance in ways that range from trivial to life threatening.

Various implantable medical devices (IMD), such as implantable pulse generators (IPG) or pacemakers and implantable cardioverter defibrillators (ICD) are utilized to control or establish particular timing parameters. Such devices typically include one or more leads that include electrodes that are electrically coupled with cardiac tissue. Electrical stimulation is delivered via these leads, but electrical signals from the heart are also sensed. The IMD utilizes the sensed data to determine what the timing parameters are, if therapy is required, and when to deliver that therapy.

Similar information can be sensed in a controlled environment by utilizing temporary leads inserted via a catheterization process. Typically, an electrophysiologist (EP) or other appropriate caregiver guides such leads through a venous or arterial pathway into the heart. Each lead may have multiple electrodes and often several leads are simultaneously employed. The leads can be positioned and repositioned as desired to "map" the electrical activity of the heart and in some cases deliver electrical stimulation for, e.g., ablation, pacing, defibrillation or even inducing arrhythmia.

With multiple leads available and with each having multiple electrodes, cardiac electrical activity can be sensed from many different locations simultaneously. For example, electrodes could sense along the atrial wall, at the AV node, along the HIS bundle, along the bundle branches (typically within the right ventricle), at the apex, and at any of a number of other locations. In addition, external sensing (i.e., ECG) data is also obtained and provides a useful reference.

In such a setting, detailed timing data can be obtained that is in excess of what is typically available from an IMD. Typically, an IMD will include two leads; one in the right atrium and one in the right ventricle. The IMD might also include a left ventricular lead and less frequently a left atrial lead. These left sided leads, if used, are typical not disposed within the left sided chamber.

DETAILED DESCRIPTION

Figure 1:
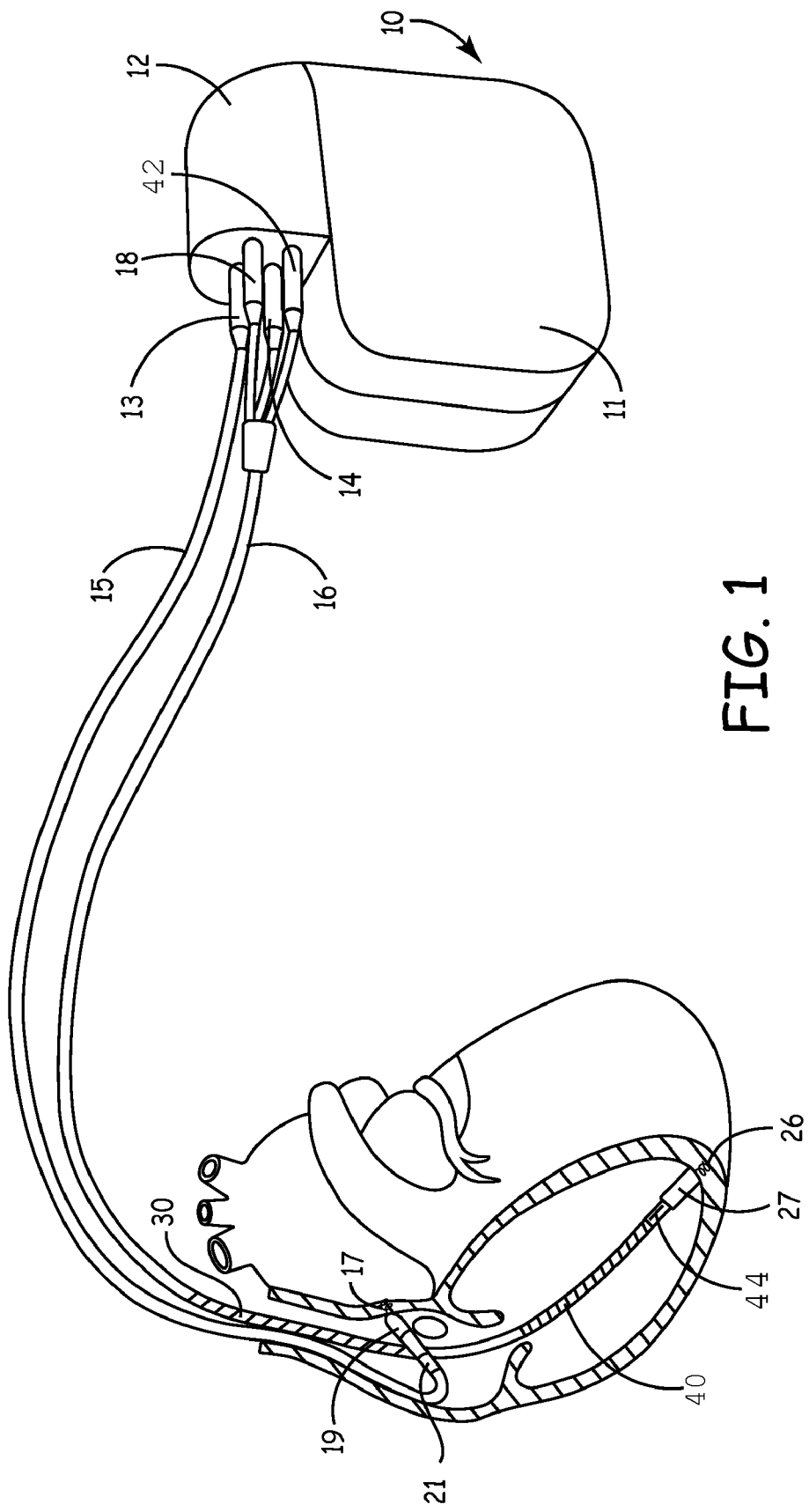
FIG. 1 is an illustration of an ICD system according to the present invention.

Referring now to FIG. 1, there are illustrated an ICD 10 and leads 15 and 16, making up the system. ICD 10 is an implantable cardioverter defibrillator. It should be appreciated that such a device may include pacing, defibrillation, cardioversion, and/or other therapies alone or in any combination. The leads shown are illustrative, it being noted that other specific forms of leads are within the scope of this invention. Ventricular lead 16 as illustrated has, located adjacent to the distal end, an extendable helix electrode 26 and a ring electrode 44, the helix electrode being mounted retractably within an insulative head 27. Electrodes 44 and 26 are used for bipolar ventricular pacing and for bipolar sensing of ventricular depolarizations. While electrodes 44 and 26 may be used for bipolar pacing and sensing, electrode 26 may be used in conjunction with the surface of device casing 10, which surface acts as a common or indifferent electrode in what is termed unipolar operation. Ventricular lead 16 also carries a coil electrode 40, sometimes referred to as the RV (right ventricular) coil, for delivering defibrillation and/or cardioversion pulses. Coil electrode 40 is positioned on lead 16 so that when the distal tip is at the apex of the ventricle, coil 40 is positioned in the right ventricle. Lead 16 may also carry, optionally, an SVC coil 30, which can be used for applying cardioversion pulses. Lead 16 carries respective concentric coil conductors (not shown), separated from one another by appropriate means such as tubular insulative sheaths and running the length of the lead for making electrical connection between the ICD device 10 and respective ones of electrodes 40, 44, 26 and 30.

Atrial lead 15 as illustrated includes an extendable helix electrode 17 and a ring electrode 21, the helix electrode being mounted retractably within an insulative head 19. Electrodes 17 and 21 are used for bipolar atrial pacing and for sensing atrial depolarizations. While electrodes 17 and 21 may be used for bipolar pacing and sensing, electrode 17 may be used in conjunction with the surface of device casing 10, which surface acts as a common or indifferent electrode in what is termed unipolar operation. Note that, in this example, atrial lead 15 is not equipped with coils for use in the sensing and delivery of cardioversion of defibrillation pulses. This is not meant to preclude the inclusion of such applications that may be used advantageously with the present invention.

An ICD device 10, is shown in combination with atrial and ventricular leads, with the lead connector assembly 13, 14, 18, and 42 being inserted into the connector block 12 of the device 10. A specific example of a defibrillation pulse generator that may be used in conjunction with the present ventricular lead is disclosed in U.S. Pat. No. 4,953,551. Other ICD type units can be used; reference is made to U.S. Pat. Nos. 5,163,427 and 5,188,105 as disclosing illustrative forms of apparatus for delivering cardioversion and defibrillation pulses. As used herein, the term "ICD type" device refers to any device that can apply both pacing therapy and shock therapy for controlling arrhythmias.

Figure 2:
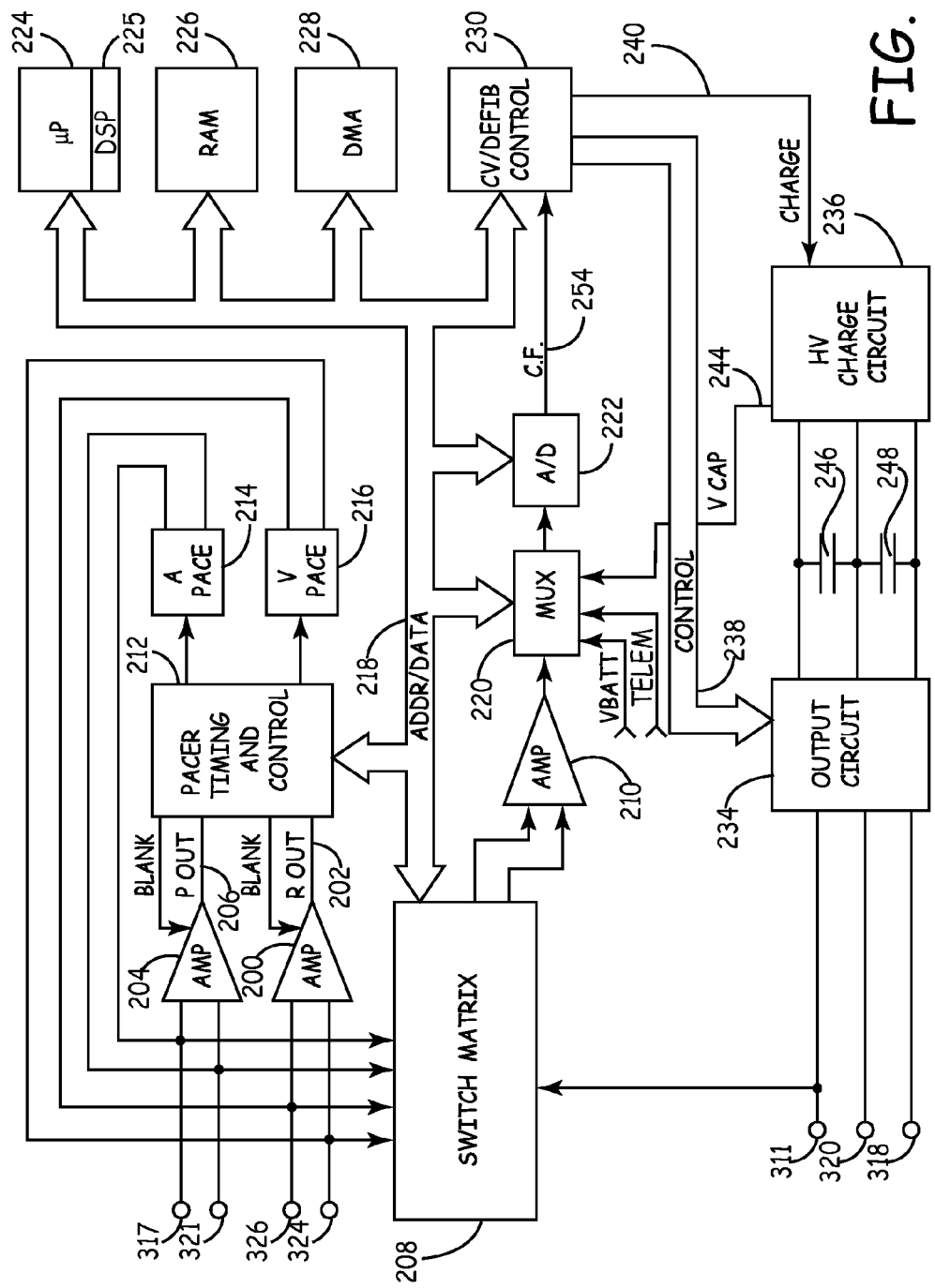
FIG. 2 is a block, functional diagram of ICD adapted to carry out the features of the present invention.

FIG. 2 is a functional schematic diagram of an implantable pacemaker/cardioverter/defibrillator in which the present invention may usefully be practiced. This diagram should be taken as exemplary of the type of device in which the invention may be embodied, and not as limiting, as it is believed that the invention may usefully be practiced in a wide variety of device implementations, including devices providing therapies for treating atrial arrhythmias instead of or in addition to ventricular arrhythmias, cardioverters and defibrillators which do not provide anti-tachycardia pacing therapies, anti-tachycardia pacers which do not provide cardioversion or defibrillation, and devices which deliver different forms of anti-arrhythmia therapies such as nerve stimulation or drug administration.

The device is provided with a lead system including electrodes, which may be as illustrated in FIG. 1. Alternate lead systems may of course be substituted. If the electrode configuration of FIG. 1 is employed, the correspondence to the illustrated electrodes is as follows. Electrode 311 corresponds to electrode 16, and is the uninsulated portion of the housing of the implantable pacemaker/cardioverter/defibrillator. Electrode 320 corresponds to electrode 40 and is a defibrillation electrode located in the right ventricle. Electrode 318 corresponds to electrode 30 and is a defibrillation electrode located in the superior vena cava. Electrodes 324 and 326 correspond to electrodes 44 and 26, and are used for sensing and pacing in the ventricle. Electrodes 317 and 321 correspond to electrodes 17 and 21 and are used for pacing and sensing in the atrium.

Electrodes 311, 318 and 320 are coupled to high voltage output circuit 234. Electrodes 324 and 326 are located on or in the ventricle and are coupled to the R-wave amplifier 200, which preferably takes the form of an automatic gain controlled amplifier providing an adjustable sensing threshold as a function of the measured R-wave amplitude. A signal is generated on R-out line 202 whenever the signal sensed between electrodes 324 and 326 exceeds the present sensing threshold.

Electrodes 317 and 321 are located on or in the atrium and are coupled to the P-wave amplifier 204, which preferably also takes the form of an automatic gain controlled amplifier providing an adjustable sensing threshold as a function of the measured P-wave amplitude. A signal is generated on P-out line 206 whenever the signal sensed between electrodes 317 and 321 exceeds the present sensing threshold. The general operation of the R-wave and P-wave amplifiers 200 and 204 may correspond to that disclosed in U.S. Pat. No. 5,117,824, by Keimel et al., issued Jun. 2, 1992, for an Apparatus for Monitoring Electrical Physiologic Signals, incorporated herein by reference in its entirety.

Switch matrix 208 is used to select which of the available electrodes are coupled to wide band (0.5-200 Hz) amplifier 210 for use in signal analysis. Selection of electrodes is controlled by the microprocessor 224 via data/address bus 218, which selections may be varied as desired. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques using DSP module 225 to characterize the digitized signals stored in random access memory 226 or provided from the A/D converter.

The remainder of the circuitry is dedicated to the provision of cardiac pacing, cardioversion and defibrillation therapies, and, for purposes of the present invention may correspond to circuitry known in the prior art. An exemplary apparatus is disclosed of accomplishing pacing, cardioversion and defibrillation functions follows. The pacer timing/control circuitry 212 includes programmable digital counters which control the basic time intervals associated with DDD, VVI, DVI, VDD, AAI, DDI and other modes of single and dual chamber pacing well known to the art. Circuitry 212 also controls escape intervals associated with anti-tachyarrhythmia pacing in both the atrium and the ventricle, employing any anti-tachyarrhythmia pacing therapies known to the art.

Intervals defined by pacing circuitry 212 include atrial and ventricular pacing escape intervals, the refractory periods during which sensed P-waves and R-waves will not restart the escape pacing interval timing. The durations of these intervals are determined by microprocessor 224, in response to stored data in memory 226 and are communicated to the pacing circuitry 212 via address/data bus 218. Pacer circuitry 212 also determines the amplitudes and pulse widths of the cardiac pacing pulses under control of microprocessor 224.

During pacing, the escape interval timers within pacer timing/control circuitry 212 are reset upon sensing of R-waves and P-waves as indicated by signals on lines 202 and 206, and in accordance with the selected mode of pacing on timeout trigger generation of pacing pulses by pacer output circuitry 214 and 216, which are coupled to electrodes 317, 321, 324 and 326. The escape interval timers are also reset on generation of pacing pulses, and thereby control the basic timing of cardiac pacing functions, including anti-tachyarrhythmia pacing. The durations of the intervals defined by the escape interval timers are determined by microprocessor 224, via data/address bus 218. The value of the count present in the escape interval timers when reset by sensed R-waves and P-waves may be used to measure the durations of R-R intervals, P-P intervals, P-R intervals, and R-P intervals, which measurements are stored in memory 226 and used in conjunction with the present invention to diagnose the occurrence of a variety of tachyarrhythmias, as discussed in more detail below.

Microprocessor 224 operates as an interrupt driven device, and is responsive to interrupts from pacer timing/control circuitry 212 corresponding to the occurrences of sensed P-waves and R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts. A portion of the memory 226 may be configured as a plurality of recirculating buffers, capable of holding series of measured intervals, which may be analyzed in response to the occurrence of a pace or sense interrupt to determine whether the patient's heart is presently exhibiting atrial or ventricular tachyarrhythmia.

The arrhythmia detection method of the ICD may include prior art tachyarrhythmia detection algorithms. As described below, the entire ventricular arrhythmia detection methodology of presently available Medtronic pacemaker/cardioverter/defibrillators is employed as part of the arrhythmia detection and classification method according to the disclosed preferred embodiment of the invention. However, any of the various arrhythmia detection methodologies known to the art, as discussed in the Background of the Invention section above might also be usefully employed in alternative embodiments of the ICD.

In the event that an atrial or ventricular tachyarrhythmia is detected, and an anti-tachyarrhythmia pacing regimen is desired, appropriate timing intervals for controlling generation of anti-tachyarrhythmia pacing therapies are loaded from microprocessor 224 into the pacer timing and control circuitry 212, to control the operation of the escape interval timers therein and to define refractory periods during which detection of R-waves and P-waves is ineffective to restart the escape interval timers. Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 7,726,380, issued to Vollmann et al. on Feb. 23, 1988 and U.S. Pat. No. 4,587,970, issued to Holley et al. on May 13, 1986, all of which are incorporated herein by reference in their entireties may also be used.

In the event that generation of a cardioversion or defibrillation pulse is required, microprocessor 224 employs the escape interval timer to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246, 248 via charging circuit 236, under control of high voltage charging control line 240. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212. Following delivery of the fibrillation or tachycardia therapy the microprocessor then returns the device to cardiac pacing and awaits the next successive interrupt due to pacing or the occurrence of a sensed atrial or ventricular depolarization.

One embodiment of an appropriate system for delivery and synchronization of ventricular cardioversion and defibrillation pulses and for controlling the timing functions related to them is disclosed in more detail in commonly assigned U.S. Pat. No. 5,188,105 by Keimel, issued Feb. 23, 1993, and incorporated herein by reference in its entirety. If atrial defibrillation capabilities are included in the device, appropriate systems for delivery and synchronization of atrial cardioversion and defibrillation pulses and for controlling the timing functions related to them may be found in PCT Pat. Application No. WO92/18198 by Adams et al., published Oct. 29, 1992, and in U.S. Pat. No. 4,316,472 by Mirowski et al., issued Feb. 23, 1982, both incorporated herein by reference in their entireties.

However, any known cardioversion or defibrillation pulse control circuitry is believed usable in conjunction with the present invention. For example, circuitry controlling the timing and generation of cardioversion and defibrillation pulses as disclosed in U.S. Pat. No. 4,384,585, issued to Zipes on May 24, 1983, in U.S. Pat. No. 4,949,719 issued to Pless et al., cited above, and in U.S. Pat. No. 4,375,817, issued to Engle et al., all incorporated herein by reference in their entireties may also be employed.

In the illustrated device, delivery of the cardioversion or defibrillation pulses is accomplished by output circuit 234, under control of control circuitry 230 via control bus 238. Output circuit 234 determines whether a monophasic or biphasic pulse is delivered, whether the housing 311 serves as cathode or anode and which electrodes are involved in delivery of the pulse. An example of output circuitry for delivery of biphasic pulse regimens may be found in the above cited patent issued to Mehra and in U.S. Pat. No. 4,727,877, incorporated by reference in its entirety.

An example of circuitry which may be used to control delivery of monophasic pulses is set forth in commonly assigned U.S. Pat. No. 5,163,427, by Keimel, issued Nov. 17, 1992, also incorporated herein by reference in its entirety. However, output control circuitry as disclosed in U.S. Pat. No. 4,953,551, issued to Mehra et al. on Sep. 4, 1990 or U.S. Pat. No. 4,800,883, issued to Winstrom on Jan. 31, 1989 both incorporated herein by reference in their entireties, may also be used in conjunction with a device embodying the present invention for delivery of biphasic pulses.

In modern implantable cardioverter/defibrillators, the physician, from a menu of therapies that are typically provided, programs the specific therapies into the device. For example, on initial detection of an atrial or ventricular tachycardia, an anti-tachycardia pacing therapy may be selected and delivered to the chamber in which the tachycardia is diagnosed or to both chambers. On redetection of tachycardia, a more aggressive anti-tachycardia pacing therapy may be scheduled. If repeated attempts at anti-tachycardia pacing therapies fail, a higher energy cardioversion pulse may be selected for subsequent delivery. Therapies for tachycardia termination may also vary with the rate of the detected tachycardia, with the therapies increasing in aggressiveness as the rate of the detected tachycardia increases. For example, fewer attempts at anti-tachycardia pacing may be undertaken prior to delivery of cardioversion pulses if the rate of the detected tachycardia is below a preset threshold. The references cited above in conjunction with descriptions of prior art tachycardia detection and treatment therapies are applicable here as well.

In the event that fibrillation is identified, the typical therapy will be the delivery of a high amplitude defibrillation pulse, typically in excess of 5 joules. Lower energy levels may be employed for cardioversion. As in the case of currently available ICDs, and as discussed in the above-cited references, it is envisioned that the amplitude of the defibrillation pulse may be incremented in response to failure of an initial pulse or pulses to terminate fibrillation. Prior art patents illustrating such pre-set therapy menus of anti-tachyarrhythmia therapies include the above-cited U.S. Pat. No. 4,830,006, issued to Haluska et al., U.S. Pat. No. 4,727,380, issued to Vollmann et al. and U.S. Pat. No. 4,587,970, issued to Holley et al.

Figure 3:
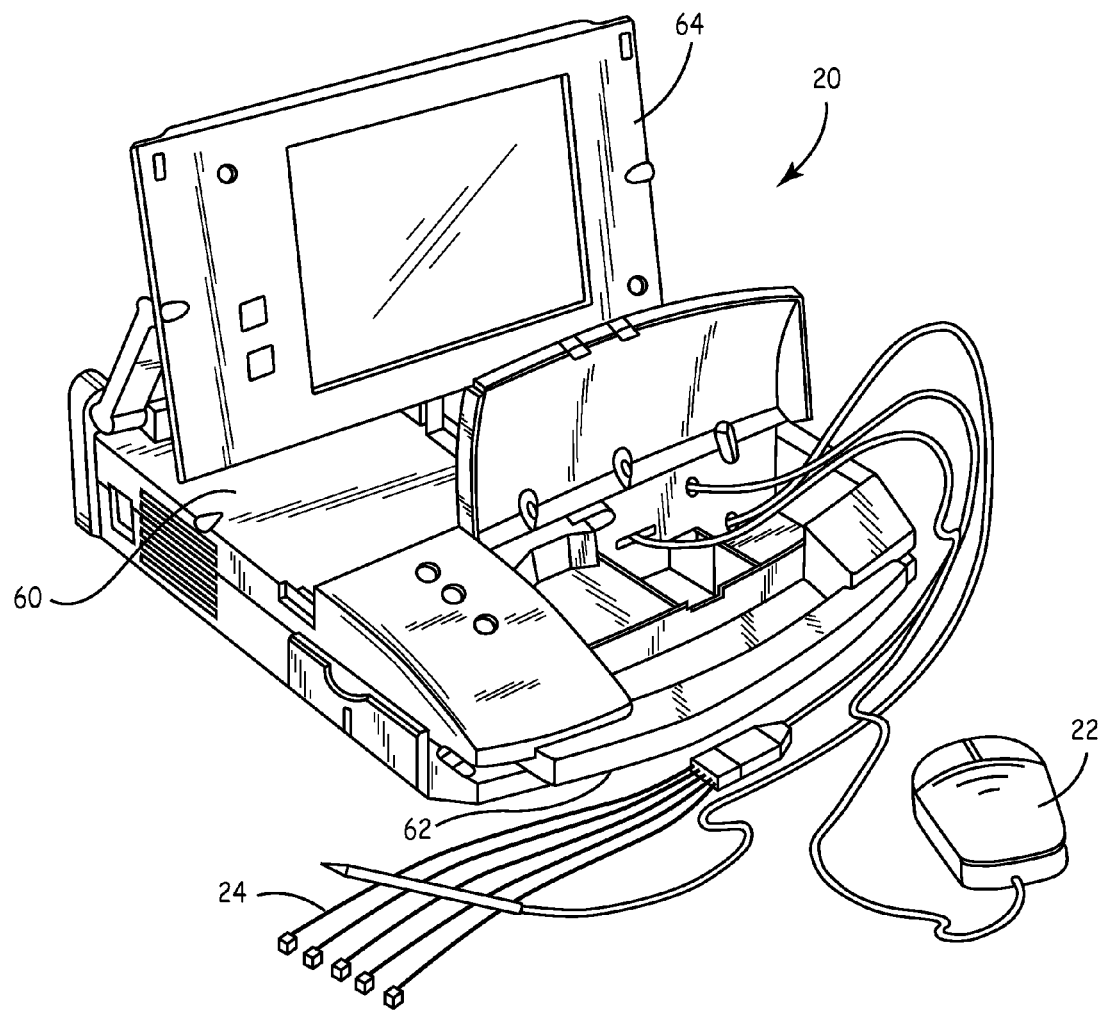
FIG. 3 is a perspective view of the external programming unit of FIG. 1.

FIG. 3 is a perspective view of programming unit program 20 in accordance with the present invention. Internally, programmer 20 includes a processing unit (not shown in the Figure) and related circuitry such as digital memory. The details of design and operation of the programmer's computer system will not be set forth in detail in the present disclosure, as it is believed that such details are well-known to those of ordinary skill in the art.

Referring to FIG. 3, programmer 20 comprises an outer housing 60, which is preferably made of thermal plastic or another suitably rugged yet relatively lightweight material. A carrying handle, designated generally as 62 in FIG. 2, is integrally formed into the front of housing 60. With handle 62, programmer 20 can be carried like a briefcase.

An articulating display screen 64 is disposed on the upper surface of housing 60. Display screen 64 folds down into a closed position (not shown) when programmer 20 is not in use, thereby reducing the size of programmer 20 and protecting the display surface of display 64 during transportation and storage thereof.

A floppy disk drive is disposed within housing 60 and is accessible via a disk insertion slot (not shown). A hard disk drive is also disposed within housing 60, and it is contemplated that a hard disk drive activity indicator, (e.g., an LED, not shown) could be provided to give a visible indication of hard disk activation.

As would be appreciated by those of ordinary skill in the art, it is often desirable to provide a means for determining the status of the patient's conduction system, heart rhythm, electrical activation and a number of other parameters. Normally, programmer 20 is equipped with external ECG leads 44.

In accordance with the present invention, programmer 20 is equipped with an internal printer (not shown) so that a hard copy of a patient's ECG or of graphics displayed on the programmer's display screen 64 can be generated. Several types of printers, such as the AR-100 printer available from General Scanning Co., are known and commercially available.

In the perspective view of FIG. 3, programmer 20 is shown with articulating display screen 64 having been lifted up into one of a plurality of possible open positions such that the display area thereof is visible to a user situated in front of programmer 20. Articulating display screen is preferably of the LCD or electro-luminescent type, characterized by being relatively thin as compared, for example, a cathode ray tube (CRT) or the like.

As would be appreciated by those of ordinary skill in the art, display screen 64 is operatively coupled to the computer circuitry disposed within housing 60 and is adapted to provide a visual display of graphics and/or data under control of the internal computer.

Programmer 20 described herein with reference to FIG. 2 is described in more detail in U.S. Pat. No. 5,345,362 issued to Thomas J. Winkler, entitled Portable Computer Apparatus With Articulating Display Panel, which patent is hereby incorporated herein by reference in its entirety. The Medtronic Model 9790 programmer is the implantable device-programming unit with which the present invention may be advantageously practiced.

Programmer 20 is generally illustrative and meant to represent any external device that receives data from the IMD 10. Such devices could be positioned proximate the patient or could include processing capabilities remotely located with respect to the patient.

Figure 4:
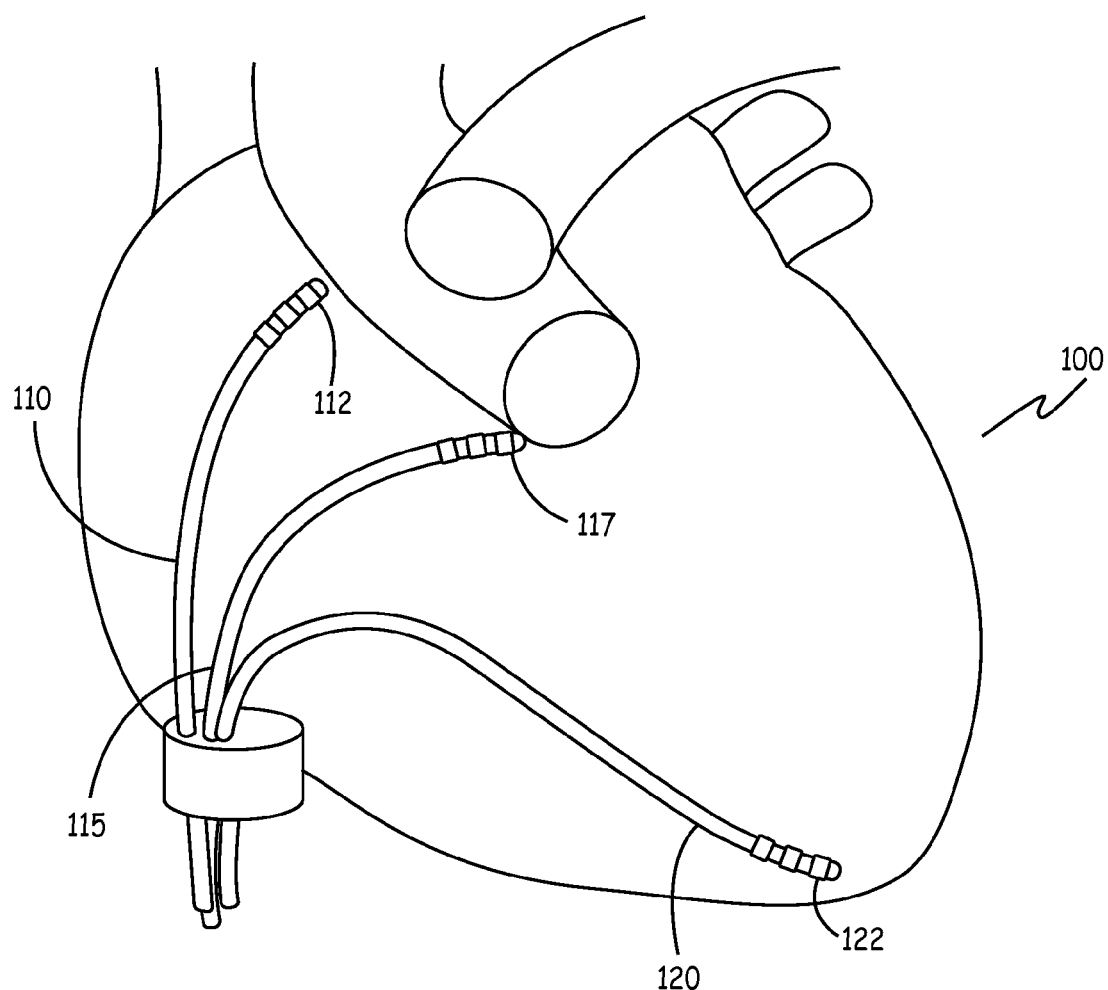
FIG. 4 is a schematic illustration of temporary leads disposed within the heart.

FIG. 4 is a cross-sectional illustration of a heart 100 having a high right atrial lead 110, a HIS lead 115 and a right ventricular lead 120 positioned within the atrial and ventricular chambers as might occur during an electrophysiology mapping procedure. The high right atrial lead 110 includes electrodes 112 in contact with cardiac tissue along the atrial wall. The HIS lead 115 includes electrodes 117 contacting cardiac tissue proximate the HIS bundle. The right ventricular lead 120 includes electrodes 122 positioned in the apex of the right ventricle.

Figure 5:
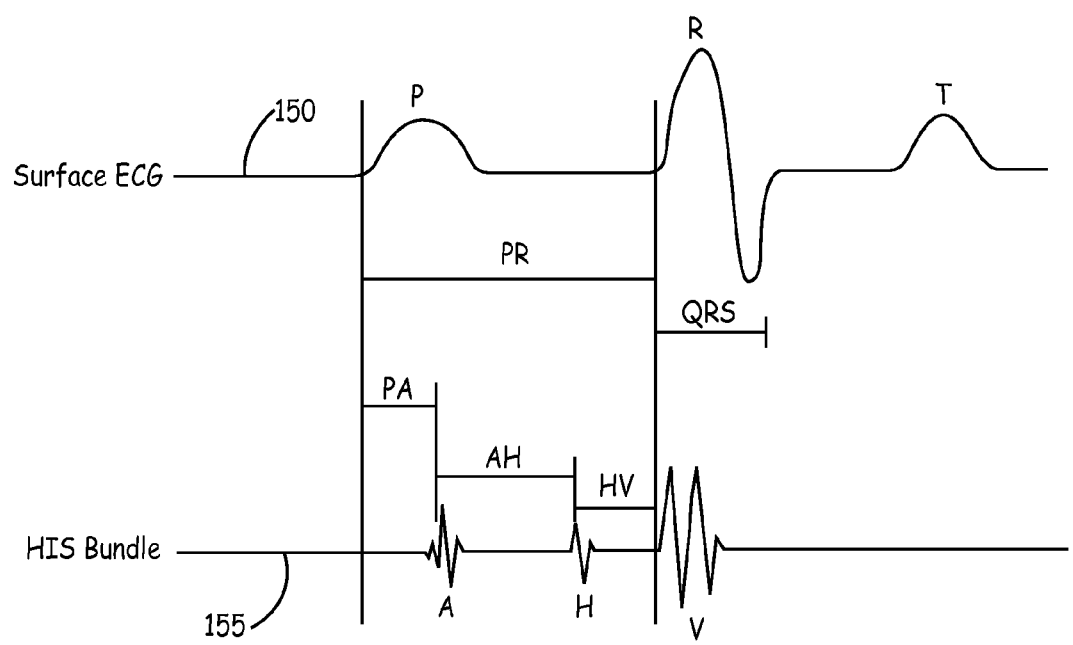
FIG. 5 is a timing diagram illustrating a representative surface ECG signal and a corresponding signal from medially disposed (HIS) lead from of FIG. 4.

FIG. 5 is an exemplary representation of a single cardiac cycle as obtained by surface ECG sensors (not shown). The ECG tracing 150 is taken as a reference point for analysis. As illustrated, the tracing includes a P wave indicative of atrial depolarization, an R wave (QRS complex) indicative of ventricular depolarization, and a T wave indicative of repolarization. Also illustrated is a HIS tracing 155 as would be produced from HIS lead 115 of FIG. 4.

With the relatively low magnitude of the P wave and the positioning of the HIS lead 115, there is some delay between the onset of atrial depolarization and its initial sense A at the HIS electrode 11. This delay is denoted as the PA interval. Between the P wave and the R wave, the HIS depolarization H occurs. That is, the HIS depolarization H is the propagation of the depolarization waterfront through the HIS bundle as it moves proximate the electrode 117. The initial sensing A is a far-field sensed event whereas the H sense is a local event. Subsequent in time, the R wave is also sensed as a far field event and denoted V. Because of the magnitude of the ventricular depolarization and the propagation speed, the HIS sense V is generally temporally proximate the ECG representation.

With the example illustrated in FIG. 5, a number of useful intervals are established. The PR interval is the timing between the onset of the atrial depolarization and the onset of the ventricular depolarization. The width of the QRS complex provides indications of, among other things, ventricular synchrony. Another useful interval is the ST segment, or the timing between the end of the QRS complex and the T wave. With the HIS lead data, the PA interval indicates the timing between the atrial depolarization and the sensing of the same on the HIS lead 115. The AH interval, is the timing between the HIS sensed atrial event and the HIS event H. Finally, the HV interval is the timing between the HIS event and the ventricular depolarization.

In the context of an electrophysiology study, the HIS timing can provide a number of useful indicators. For example, such timing may indicate conduction delay or block as well as the source of that delay or block. The difficulty with obtaining such information is the requirement for the HIS lead as well as the fact that such leads, when utilized, are not typically anchored. Thus, without a fixed location, the potential exists for inconsistent measurements. Another difficulty with EP studies is that they are localized in time. That is, conditions may or may not be present during the study and such conditions may develop over time. As such, conditions indicated by HIS timing variations may well be overlooked outside the scope of an EP study. Therefore, HIS timing is not available to IMDs that do not typically include a HIS lead.

Referring to FIG. 1, a typical two lead configuration (e.g., atrial lead 15 and ventricular lead 16) is presented that allows for HIS timing to be acquired. It should be appreciated that other lead configurations for IMDs may also be utilized the manner described. Referring also to FIG. 4, IMD leads 15 and 16 are positioned in a manner similar to EP leads 110 and 120.

Figure 6:
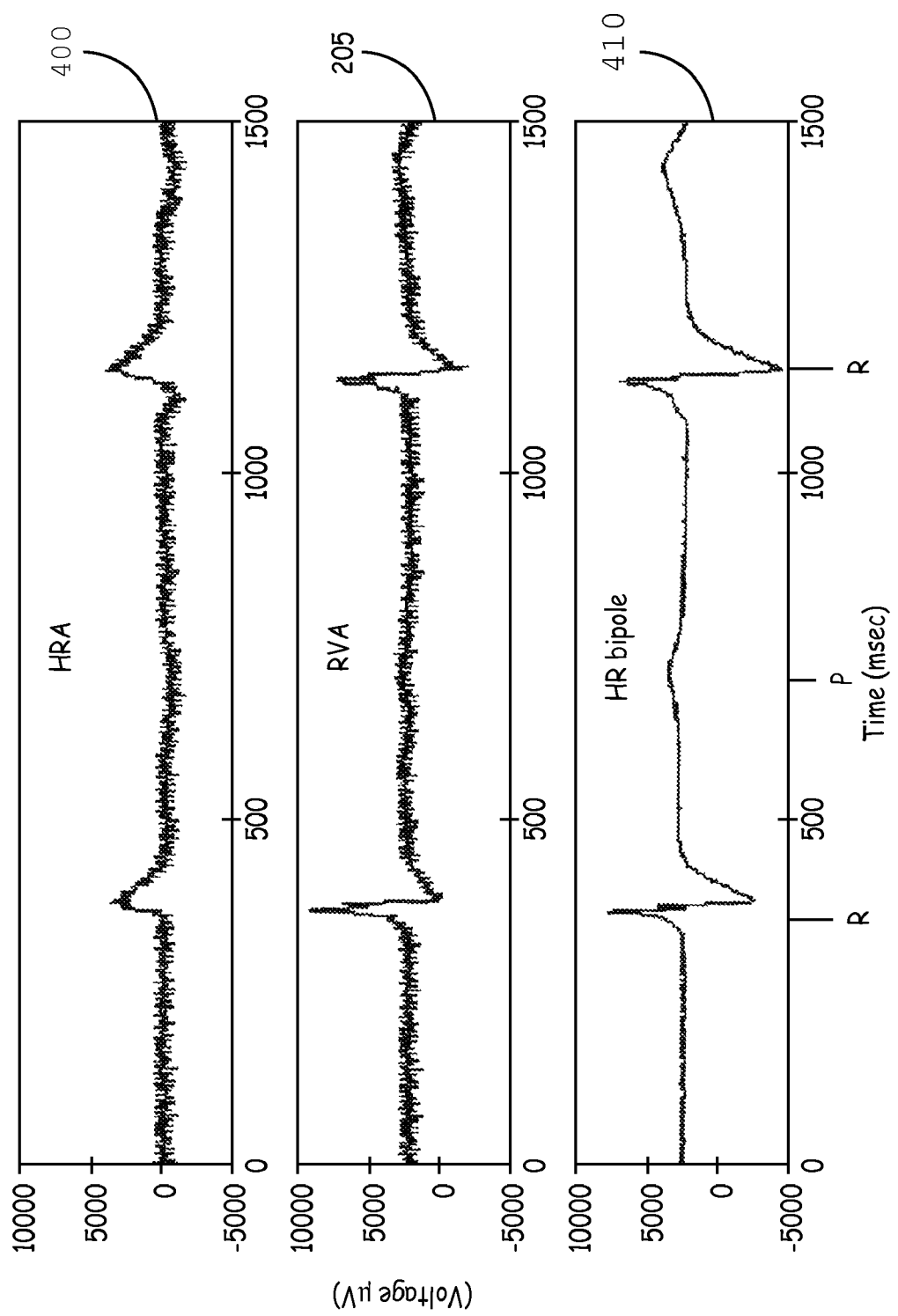
FIG. 6 is a diagram illustrating atrial and ventricular signal and a signal representing the atrial signal minus the ventricular signal.

The HIS signal is identified in this two lead arrangement by subtracting the ventricular lead signal from the atrial lead signal. FIG. 6 illustrates a graph including an HRA (high right atrial) output 400 from the atrial lead 15, a RVA (right ventricular apex) output 205 from the ventricular lead 16 and the HIS signal 410 which is the RVA output 205 subtracted from the HRA output 400. In this graph, no HIS activity is visible. Two R waves and a P wave are indicated as marked.

Figure 7:
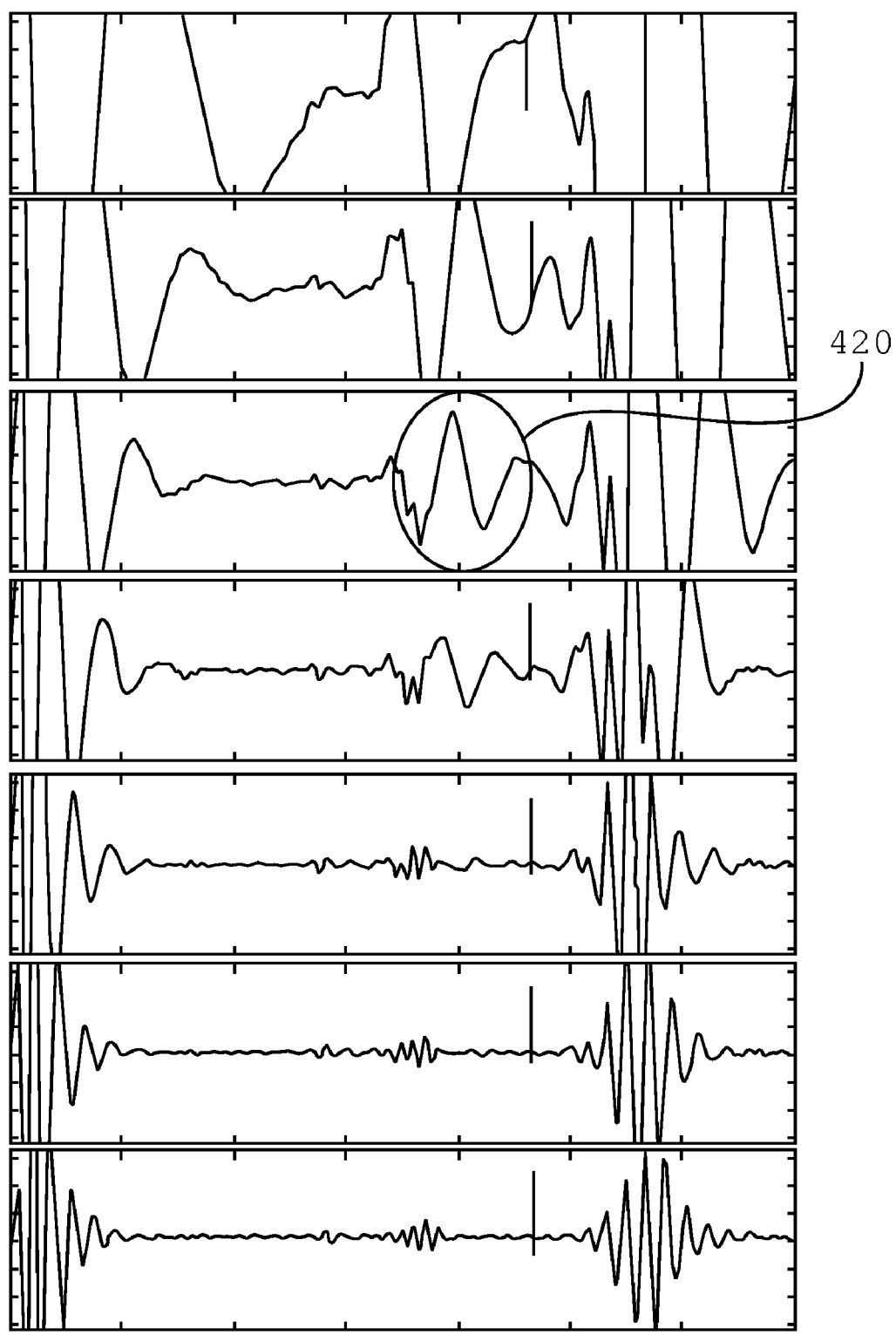
FIG. 7 is a series if processed signals illustrating a variety of band pass filter effects.
Figure 8:
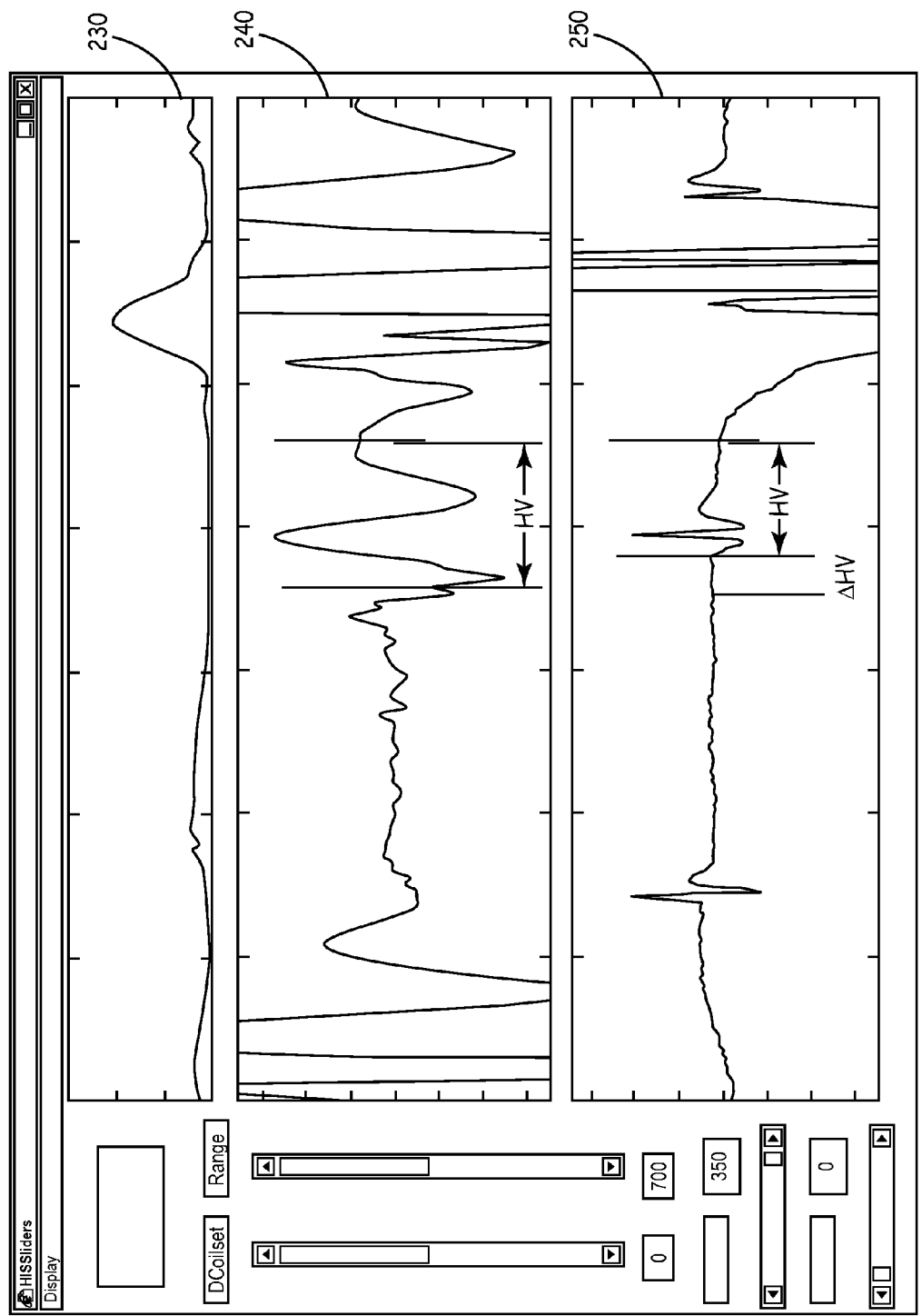
FIG. 8. illustrates a comparison of derived HIS data and directly acquired HIS data from a HIS lead.

The HIS signal 410 is then passed through a bandpass filter. FIG. 7 illustrates the effects of a variety of different filters on the signal. A 30 Hz filter, in this example, produced a good representation of HIS activity 420. FIG. 8. Illustrates a graph comparing surface ECG data 230, HIS signal data 240, and HIS electrode data 250. In particular, the HV intervals are defined. That is, the time interval from the initiation of HIS activity to the initiation of ventricular activity. The derived HIS data 240 is consistent with the data collected from a HIS electrode.

In one embodiment, digital signal processing (DSP) is utilized to derive the HIS signal 410. The analog atrial and ventricular signals are sampled at a rate of 1 kHz and encoded in a 12 bit format prior to processing.

While it is possible to perform such an analysis real time on a beat-to-beat basis with sufficient processing capability, HIS timing data is also useful as a trended data set or as various points in time measurements. In such cases, accuracy may be further improved by accumulating data over multiple cardiac cycles. Furthermore, in certain IMDs, processing capabilities may be limited and/or the additional power consumption required from a battery might not justify real time processing in some cases.

Figure 9:
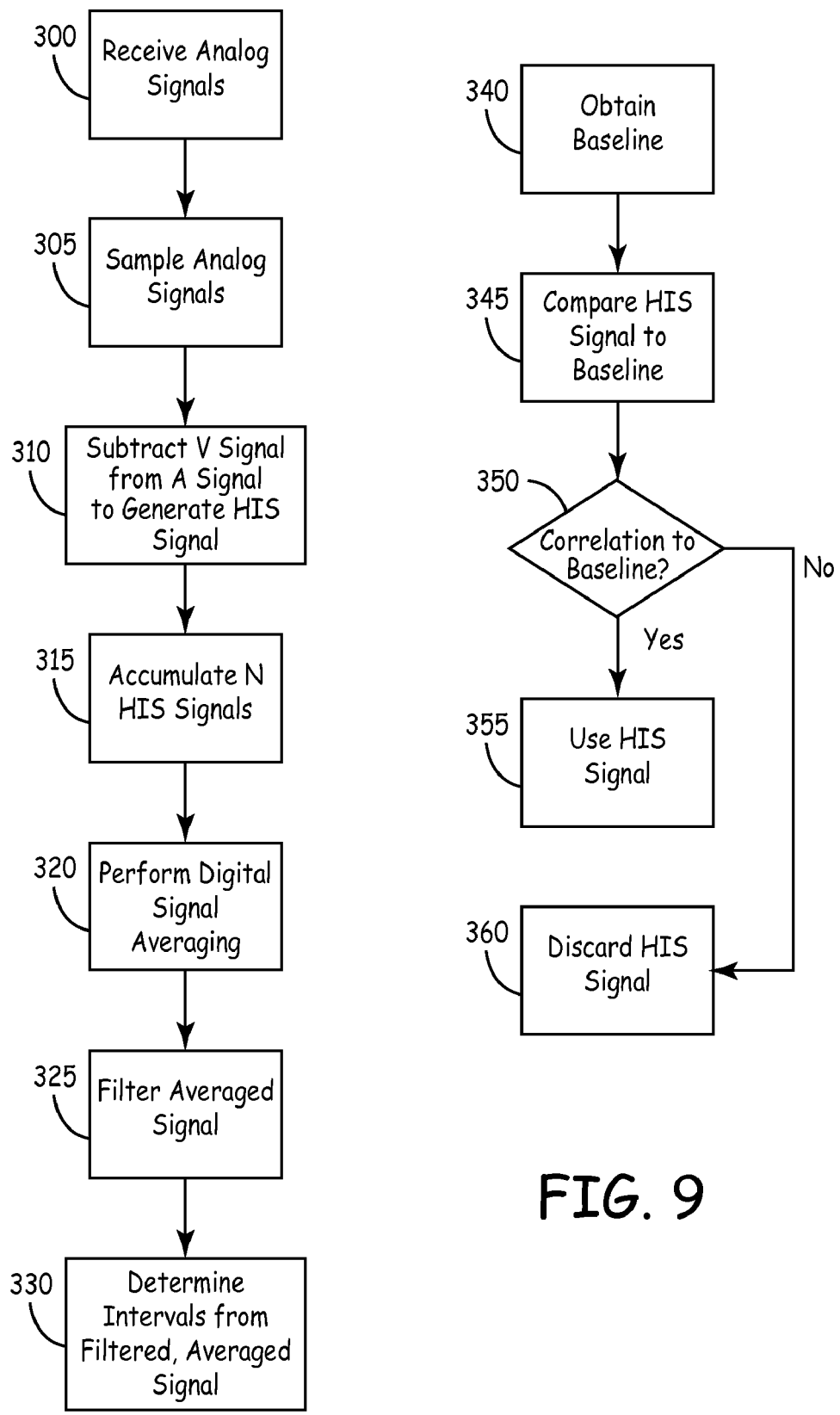
FIG. 9 is a flowchart illustrating a process for acquiring HIS data.

FIG. 9 is a flowchart illustrating a process for determining HIS timing from leads distant from the HIS bundle. For example, an IMD having an atrial lead and a ventricular lead collects (300) analog data representative of electrical activity sensed proximate to electrodes coupled with the leads. The analog data include both local and far-field events along with noise from numerous sources.

The analog signals are sampled (305) by, e.g., A/D converter 222 and converted into digital data. The sampling rate and quality should be sufficient to permit identification of the HIS data. In one embodiment, the A/D converter 222 samples at 1 kHz and at 12 bits per sample. The converted signals are subtracted (310), e.g., the ventricular signal is subtracted from the atrial signal. The resultant signal is referred to as the HIS signal. With real time, beat-to-beat processing, this HIS signal is analyzed to identify HIS timing.

Alternatively, a given number (N) of HIS signals are acquired (315) and these signal are averaged (320) together using any known signal averaging technique. The averaged signal is then filtered (325). For example, a 30 Hz bandpass filter is used on one embodiment. From the filtered, averaged signal HIS electrical activity is identified (330) and the desired intervals can be measured. For example, the AH (PH) interval, the HV interval, the AV interval, and width or duration of the H activity can be measured. As previously described with reference to FIG. 5, the AH interval occurred between the HIS lead sensed atrial activity (A) and the HIS lead sensed HIS activity (H). In the present embodiment, the atrial activity is obtained from the atrial lead and thus would approximate the PA+AH interval illustrated in FIG. 5. Thus, this interval may be referred to as either the AH interval or the PH interval in this context.

Further illustrated in FIG. 9 is an optional subroutine that may be utilized to further improve accuracy. Initially, a baseline QRS complex is acquired and sampled (340). The baseline QRS complex will be used to compare subsequently obtained data; thus, the baseline complex may itself be averaged from a number of samples or multiple samples may be acquired and otherwise analyzed to determine that the baseline complex represents a "typical" cardiac cycle.

Once the baseline is obtained, each subsequently acquired HIS signal is compared (345) with this baseline. If the HIS signal correlates well with the baseline, then the HIS signal is utilized (355); if not, the HIS signal is discarded (360). Correlation (350) may be determined in a number of ways includes temporal alignment. That is, the compared complex (e.g., QRS complex) from each signal will be temporally aligned within a predetermined variance of e.g., 10%.

Depending upon the intervals selected for HIS measurements over time, sampled HIS signals may be collected during different activity levels for the patient. Thus, multiple baselines may be established. For example, one baseline may relate to a resting rate (e.g., approximately 60 bpm) while one or more other baselines may be correlated with elevated activity levels. Thus, the HIS is compared to a baseline relevant to the heart rate during which the HIS signal was acquired.

In addition to variations in activity and heart rate, other activities may occur that would include separate baseline data. For example, the patient may periodically have various arrhythmias such as atrial fibrillation or flutter, bradycardia, etc. that result in a different "typical" complex when occurring. As such, establishing a baseline during these conditions will allow the HIS timing to continue to be acquired and may be utilized in analyzing the arrhythmia or delivering therapy.

As indicated, the baseline should be representative of a typical cycle for the patient. As data is acquired over time, HIS signal may correlate with less frequency to the baseline. This may be used as a trigger to reacquire the baseline.

Various embodiments of the invention have been described. These and other embodiments are within the scope of the following claims.

The invention claimed is:

1. An implantable medical device (IMD) comprising:
   means for acquiring analog signals from cardiac activity;
   means for converting the analog signals to digital signals;
   means for processing the digital signals to identify HIS bundle electrical timing wherein the means for processing include means for subtracting a ventricular signal from an atrial signal to produce a HIS signal; and
   means for computing intervals between the HIS signal and each of the ventricular and atrial signals;
   means for determining the performance of the conduction system based on the monitored intervals.

2. The IMD of claim 1, wherein the means for acquiring include an atrial lead and a ventricular lead.

3. The IMD of claim 1, further comprising means for filtering the HIS signal.

4. The IMD of claim 3, wherein the means for filtering include a bandpass filter.

5. The IMD of claim 4, wherein the bandpass filter is a 30 Hz bandpass filter.

6. The IMD if claim 1, further comprising means for averaging multiple HIS signals.

7. The IMD of claim 1, where the means for converting include a 12 bit A/D converter sampling at a rate of 1 kHz or greater.

8. An implantable medical device (IMD) comprising:
   a processor;
   an atrial lead electrically coupled with the processor and providing analog atrial data to the processor;
   a ventricular lead electrically coupled with the processor and providing analog ventricular data to the processor;
   an A/D converter in electrical communication with the processor for converting the analog atrial data and analog ventricular data to digital atrial data and digital ventricular data; and
   a digital signal processing module in communication with the processor, said digital signal processing module including an algorithm to subtract the ventricular signal defined by the digital ventricular data from an atrial signal defined by the digital atrial data to produce a HIS signal, wherein intervals between the HIS signal and each of the ventricular and atrial signals is monitored to determine the performance of the conduction system based on the monitored intervals.

9. A method of determining timing within a HIS bundle from an atrial and a ventricular lead, the method comprising:
  sensing electrical activity within a ventricle via the ventricular lead;
  sensing electrical activity with an atrium via the atrial lead;
  sampling the sensed electrical activity from the atrium and from the ventricle to produce an atrial signal and a ventricular signal;
  subtracting the ventricular signal from the atrial signal to produce a HIS signal;
  identifying the timing of HIS electrical activity from the HIS signal; and
  averaging a plurality of the identified HIS signals to establish a baseline signal;
  utilizing the baseline signal to analyze a subsequent HIS signal, wherein the analysis includes monitoring intervals between the HIS signal and each of the ventricular and atrial signals to determine the performance of the conduction system.

10. The method of claim 9, further comprising averaging a plurality of HIS signals prior to identifying the timing.

11. The method of claim 9, further comprising filtering the HIS signal prior to identifying the timing.

12. The method of claim 9, further comprising:
  generating a baseline complex;
  comparing the HIS signal to the baseline; and
  discarding the HIS signal unless the HIS signal is temporally correlated to the baseline.

\* \* \* \* \*